United States Patent
Fung et al.

(10) Patent No.: US 7,689,263 B1
(45) Date of Patent: Mar. 30, 2010

(54) METHOD AND APPARATUS FOR ACQUIRING FREE-BREATHING MR IMAGES USING NAVIGATOR ECHO WITH SATURATION RF PULSE

(75) Inventors: Maggie M. Fung, Mountville, PA (US); Thomas K. F. Foo, Potomac, MD (US)

(73) Assignee: General Electric Company, Schenectady, NY (US)

(*) Notice: Subject to any disclaimer, the term of this patent is extended or adjusted under 35 U.S.C. 154(b) by 1231 days.

(21) Appl. No.: 11/162,589

(22) Filed: Sep. 15, 2005

(51) Int. Cl.
*A61B 5/05* (2006.01)
*G01V 3/00* (2006.01)

(52) U.S. Cl. .................. 600/410; 600/413; 324/307

(58) Field of Classification Search .......... 600/420, 600/410, 419, 529, 411, 413, 407; 324/306, 324/307–309
See application file for complete search history.

(56) References Cited

U.S. PATENT DOCUMENTS

| | | | | |
|---|---|---|---|---|
| 4,715,383 A | * | 12/1987 | Ehman et al. ............... | 600/410 |
| 4,968,935 A | * | 11/1990 | Ehman et al. ............... | 324/309 |
| 5,510,713 A | * | 4/1996 | Bernstein .................... | 324/309 |
| 6,167,293 A | * | 12/2000 | Chenevert et al. .......... | 600/420 |
| 6,369,568 B1 | * | 4/2002 | Ma et al. .................... | 324/309 |

OTHER PUBLICATIONS

Koktzoglou et al., Coronary Artery Wall Imaging: Initial Experience at 3 Tesla, Journal of Magnetic Resonance Imaging, 2005, pp. 128-132, No. 21, Publisher: Wiley-Liss, Inc.

* cited by examiner

*Primary Examiner*—Eric F Winakur
*Assistant Examiner*—Lawrence N Laryea
(74) *Attorney, Agent, or Firm*—Ziolkowski Patent Solutions Group, SC (57) ABSTRACT

A system and method of free-breathing MR imaging saturates an entire navigator profile at the end of an imaging segment of physiological motion cycle, e.g., heart cycle, thereby providing a uniform recovery of longitudinal magnetization for the next imaging cycle. Through use of at least one dephaser gradient following the image acquisition segment and a navigator RF saturation pulse, residual transverse magnetization is dephased and spins within a navigator tracker are saturated to ensure a uniform recovery of longitudinal magnetization for the next imaging period.

25 Claims, 5 Drawing Sheets

METHOD AND APPARATUS FOR ACQUIRING FREE-BREATHING MR IMAGES USING NAVIGATOR ECHO WITH SATURATION RF PULSE

BACKGROUND OF THE INVENTION

The present invention relates generally to magnetic resonance (MR) imaging and, more particularly, to a method and apparatus of acquiring MR data from a motion tracker and gating acquisition of free-breathing MR images.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Magnetic resonance imaging is frequently used to acquire MR images of the cardiac and abdominal regions of a patient. A concern faced with cardiac and abdominal imaging is the impact of patient breathing. That is, patient breathing often contributes to motion artifacts in the image. As a result, a number of MR scans are conducted during intervals of patient breath-holds. By acquiring data during breath-holds, patient motion can be reduced and, therefore, artifacts reduced.

Requiring patient breath-holding during an MR scan has a number of drawbacks. For example, extensive and repetitive breath-hold moments can lead to patient discomfort and fatigue, in addition to an increasing inability to maintain further breath-holding. Also, breath-holding is generally patient dependent and therefore the physical condition and limitations of a given patient may limit the MR scan. In other words, breath-holding time limits the spatial resolution and number of slices that can be acquired. This can be particularly problematic for 3D imaging. That is, patients are often unable to suspend breathing for the time necessary for routine 3D scans.

Thus, as an alternative to breath-holding, respiratory gating techniques have been developed to prospectively or retrospectively gate the acquisition of MR data such that free-breathing can occur during data acquisition. One such gating technique is generally referred to navigator echo imaging. This technique is used to directly detect the position of the right hemi-diaphragm and uses the positional information to gate data acquisition from a free-breathing patient. Specifically, a spin echo sequence with perpendicularly intersecting slab planes or a cylindrical excitation gradient echo sequence is used to selectively excite a column of spins. The position of the column is generally perpendicular to the dome of the right hemi-diaphragm, the anterior left ventricle wall, or other locations where respiratory or other motion can be captured. Post-processing of the resulting echo yields the position of the tracked object, which can be used as a basis for navigator gating.

Figure 1:
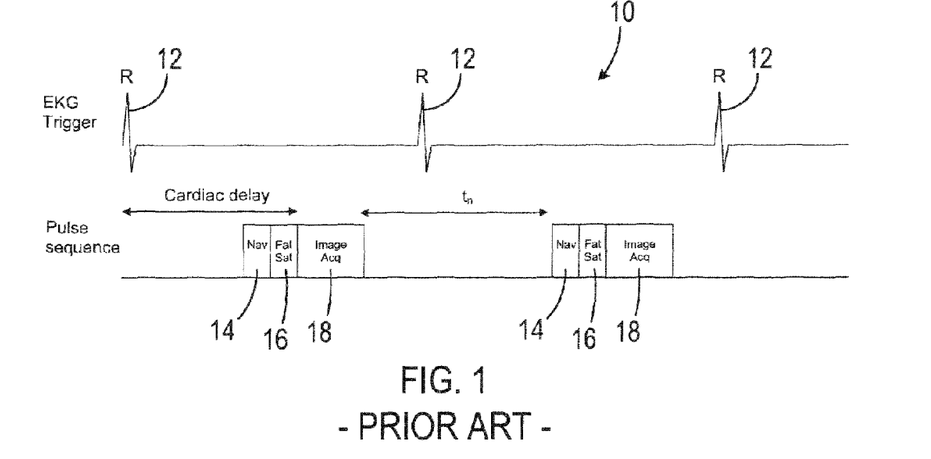
FIG. 1 illustrates a sequence diagram for a conventional ECG gated, navigator gated, fat sat, segmented 3D FGRE/FIESTA sequence.

A conventional navigator echo pulse sequence is illustrated in FIG. 1. Specifically, FIG. 1 illustrates the sequence diagram of a conventional electrocardiogram (ECG) gated, navigator gated, fat suppressed (saturation), segmented 3D FGRE/FIESTA sequence. As illustrated, the pulse sequence is triggered by an ECG trigger signal 10 that is defined by R peaks 12. The time interval between the R-wave peaks define the periodic cardiac (R-R) interval. With this conventional MR pulse sequence, data is acquired after a period of cardiac delay. Following the period of cardiac delay, a navigator excitation pulse 14 is played out to sample a navigator echo. This navigator excitation is followed by a fat saturation segment 16. Thereafter, a segmented part of k-space is acquired during imaging acquisition segment 18. These segments 14, 16, and 18 repeat each heart cycle, i.e., each R-R interval, until all the k-space views have been acquired.

Figure 2:
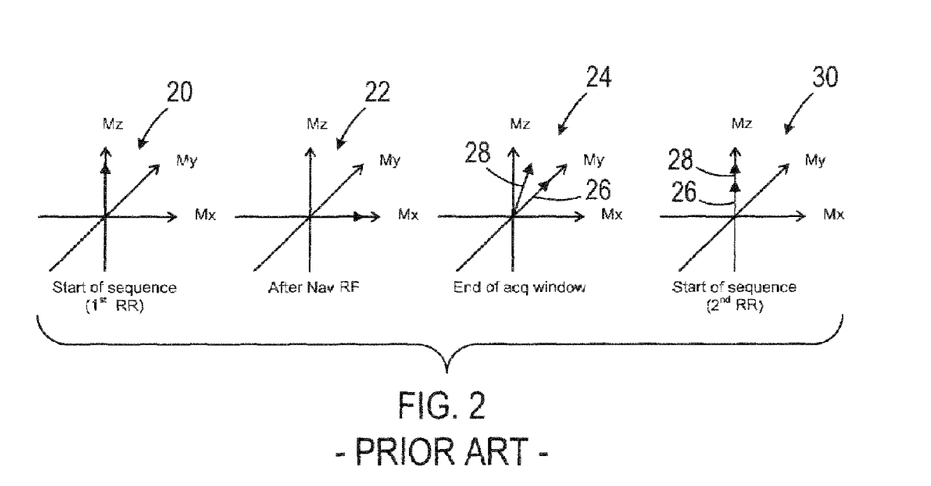
FIG. 2 illustrates the evolution of magnetization of overlapped and non-overlapped spins within a navigator tracker at different time points within two consecutive heart cycles resulting from application of the pulse sequence illustrated in FIG. 1.
Figure 3:
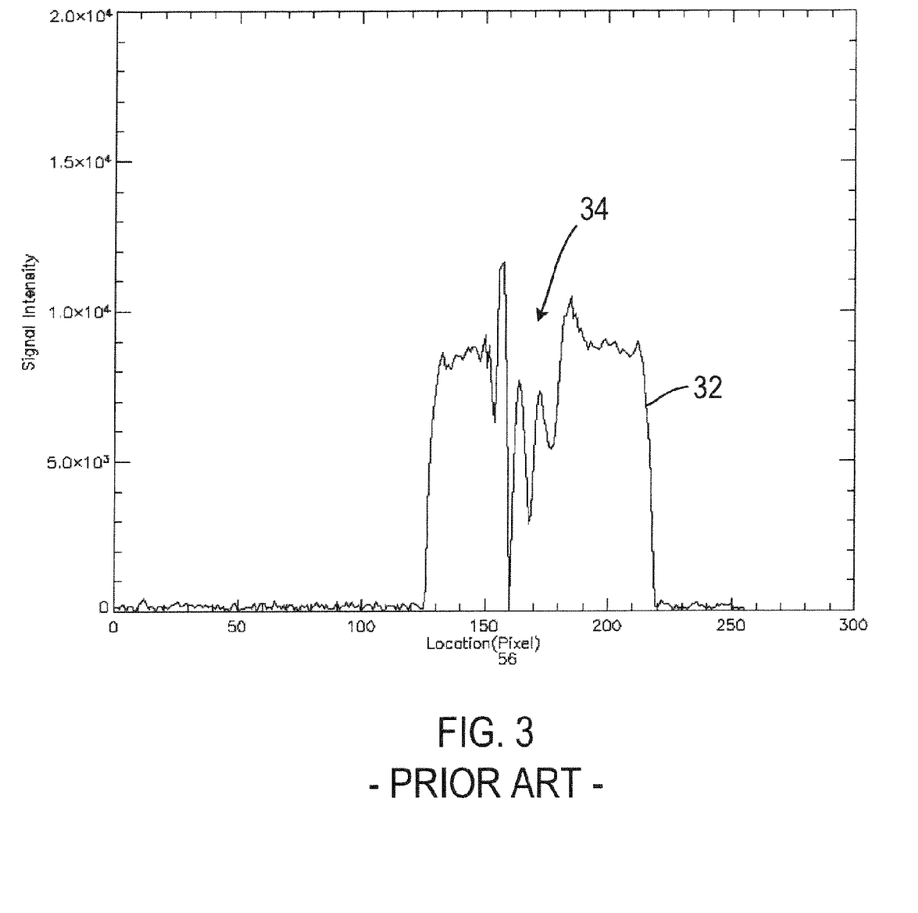
FIG. 3 is a signal intensity profile for the navigator tracker during the second heart cycle of two consecutive heart cycles resulting from application of the pulse sequence illustrated in FIG. 1.

In the case of whole heart imaging or liver imaging, an axial imaging slab is generally defined across the entire heart or liver and the navigator tracker is defined at the right hemi-diaphragm of the patient. This conventional placement, however, poses a problem for quality of the navigator tracker profile because it is partially overlapped by the axial imaging slab, as illustrated in FIG. 2. During the first heart cycle, after the navigator saturation pulse and the fat saturation pulses have been applied 20 and 22, respectively, the k-space segment acquisition for the first heart cycle is acquired 24. After this acquisition segment is complete, some of the spins within the navigator tracker column will be saturated by the excitation RF pulse defining the imaging slab whereas other spins will not. Line 26 corresponds to the magnetization of the overlapped spins whereas line 28 corresponds to the non-overlapped spins. As all the spins recover at the same rated based on their longitudinal magnetization left at the end of the k-space segment ($M'_z$), at the beginning of the acquisition at the next heart cycle 30, the spins within the navigator tracker column will be recovered to:

$$M_z(t_n) = M'_z \exp(-t_n/T_1) + M_o(1 - \exp(-t_n/T_1))$$ (Eqn. 1), where $M_z(t_n)$ is the longitudinal magnetization at time $t_n$, $t_n$ is the time from the navigator saturation RF excitation pulse to the navigator saturation RF excitation pulse of the next heart cycle, $M'_z$ is the longitudinal magnetization present immediately after the image acquisition, $M_0$ is the equilibrium longitudinal magnetization, and $T_1$ is the spin-lattice relaxation time of the tissue/blood. As the residual longitudinal magnetization ($M'_z$) is lower in the area overlapped by the imaging slab, the signal intensity in those areas (proportional to $M_z(t)$) will be reduced and the shape of the navigator profile will be distorted. Most motion detection techniques such as edge detection, least-squares error minimization, and cross-correlation are sensitive to the shape of the profile. Therefore, the motion detection accuracy will be reduced and the image quality of the resulting image will be degraded by motion artifact. FIG. 3 illustrates the navigator spatial profile 32 at the second heart cycle. As illustrated, the reduction in longitudinal magnetization in spins within the imaging slab results in a significant signal intensity drop at the area intersected by the imaging slab 34.

It would therefore be desirable to have a system and method capable of navigator echo tracking with patient free-breathing that is less susceptible to the saturation effect on the shape of the signal intensity profile described above.

BRIEF DESCRIPTION OF THE INVENTION

The present invention provides a system and method of free-breathing MR imaging that overcomes the aforementioned drawbacks by saturating the entire navigator profile at the end of the imaging segment of physiological motion cycle, e.g., heart cycle, thereby providing a uniform recovery of longitudinal magnetization for the next imaging cycle. Through judicious use of dephaser gradients following the image acquisition segment and a navigator RF saturation pulse, residual transverse magnetization is appropriately dephased and spins within a navigator tracker are saturated to ensure a uniform recovery of longitudinal magnetization for the next imaging period along the entire length of the navigator column. That is, all spins within the navigator or tracker column are saturated and recover from the same longitudinal magnetization ($M_z=0$), irrespective of position in the navigator or tracker column.

Therefore, in accordance with one aspect of the present invention, an MR imaging apparatus is disclosed and includes a plurality of gradient coils positioned about a bore of a magnet to impress a polarizing magnetic field and an RF transceiver system and an RF switch controlled by a pulse module to transmit RF signals to an RF coil assembly to acquire MR images. The apparatus also has a computer programmed to apply a pulse sequence during an imaging period of a free-breathing grated acquisition. The pulse sequence is defined by a navigator RF excitation pulse designed to selectively excite a tracker (navigator) column and an image acquisition segment designed to acquire MR data. The pulse sequence also has a navigator RF saturation pulse designed to saturate the tracker column such that longitudinal magnetization recovery in the tracker column is uniform for a next imaging period.

In accordance with another aspect, the present invention includes a method of MR imaging that includes the steps of (A) applying an RF excitation pulse to excite spins within a tracker portion of a subject to be imaged and (B) applying an imaging sequence to acquire MR data from a region-of-interest. The method further includes the steps of (C) applying an RF saturation pulse to saturate spins within the tracker portion after acquisition of the MR data and (D) repeating steps (A)-(C) in each cycle of a physiologically gated acquisition.

In accordance with another aspect of the invention, the invention is embodied in a computer program stored on a computer readable storage medium and having instructions which, when executed by a computer, cause the computer to acquire tracking data from a motion tracker and acquire imaging data for a segment of k-space from a region-of-interest. The computer is further caused to suppress residual longitudinal magnetization in the motion tracker and repeat the acquisition of tracking data and imaging data and suppression of longitudinal magnetization every cycle of a gated acquisition until the necessary k-space is acquired.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 4:
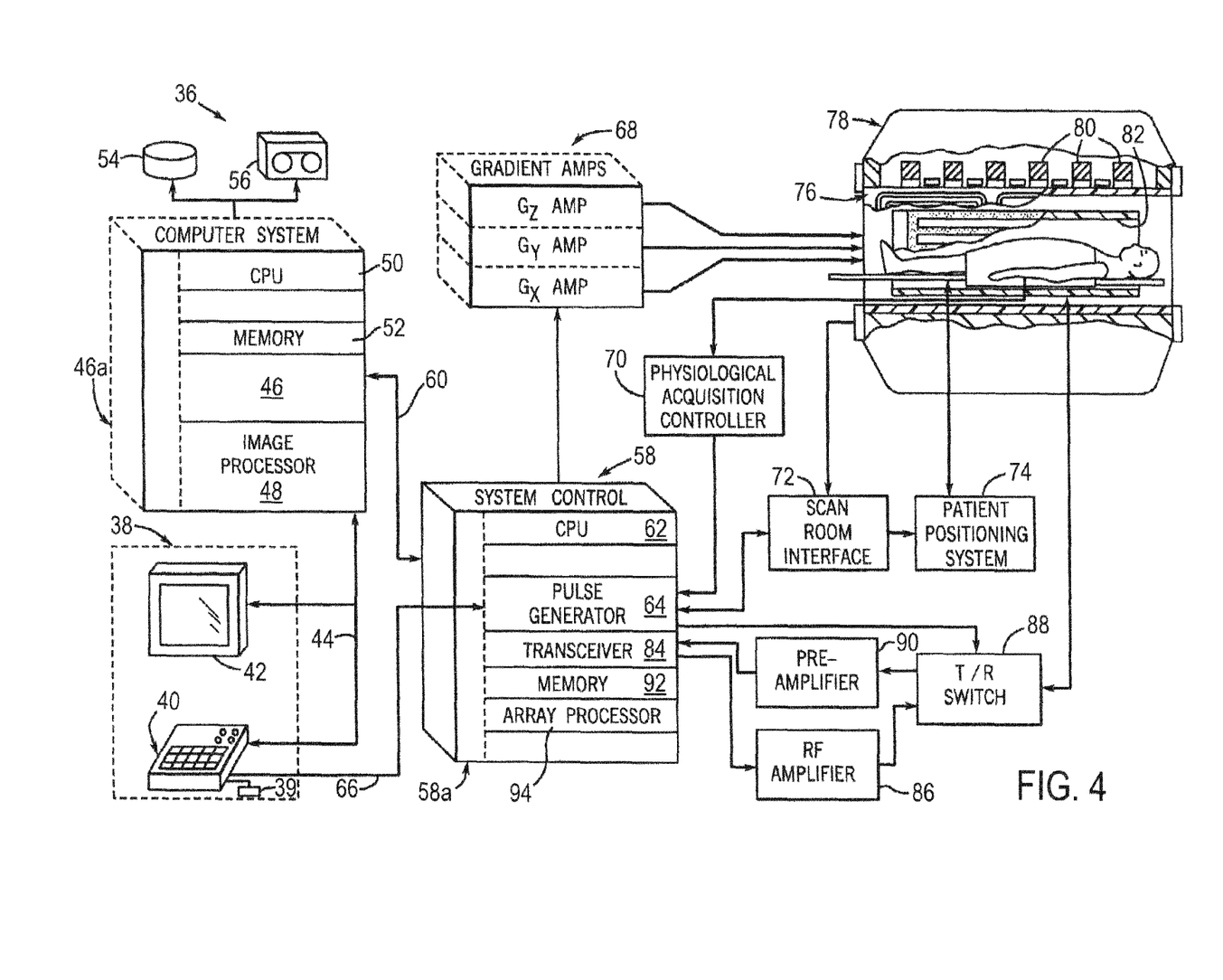
FIG. 4 is a schematic block diagram of an MR imaging system for use with the present invention.

Referring to FIG. 4, the major components of a preferred MR apparatus 36 incorporating the present invention are shown. The operation of the system is controlled from an operator console 38 which includes a keyboard or other input device 39, a control panel 40, and a display screen 42. The console 38 communicates through a link 44 with a separate computer system 46 that enables an operator to control the production and display of images on the display screen 72. The computer system 46 includes a number of modules which communicate with each other through a backplane 46a. These include an image processor module 48, a CPU module 50 and a memory module 52, known in the art as a frame buffer for storing image data arrays. The computer system 46 is linked to disk storage 54 and tape drive 56 for storage of image data and programs, and communicates with a separate system control 58 through a high speed serial link 60. The input device 39 can include a mouse, joystick, keyboard, track ball, touch activated screen, light wand, voice control, or any similar or equivalent input device, and may be used for interactive geometry prescription.

The system control 58 includes a set of modules connected together by a backplane 58a. These include a CPU module 62 and a pulse generator module 64 which connects to the operator console 38 through a serial link 66. It is through link 66 that the system control 58 receives commands from the operator to indicate the scan sequence that is to be performed. The pulse generator module 64 operates the system components to carry out the desired scan sequence and produces data which indicates the timing, strength and shape of the RF pulses produced, and the timing and length of the data acquisition window. The pulse generator module 64 connects to a set of gradient amplifiers 68, to indicate the timing and shape of the gradient pulses that are produced during the scan. The pulse generator module 6 can also receive patient data from a physiological acquisition controller 70 that receives signals from a number of different sensors connected to the patient, such as ECG signals from electrodes attached to the patient. And finally, the pulse generator module 64 connects to a scan room interface circuit 72 which receives signals from various sensors associated with the condition of the patient and the magnet system. It is also through the scan room interface circuit 72 that a patient positioning system 74 receives commands to move the patient to the desired position for the scan.

The gradient waveforms produced by the pulse generator module 64 are applied to the gradient amplifier system 67 having Gx, Gy, and Gz amplifiers. Each gradient amplifier excites a corresponding physical gradient coil in a gradient coil assembly generally designated 76 to produce the magnetic field gradients used for spatially encoding acquired signals. The gradient coil assembly 76 forms part of a magnet assembly 78 which includes a polarizing magnet 80 and a whole-body RF coil 82. A transceiver module 84 in the system control 58 produces pulses which are amplified by an RF amplifier 86 and coupled to the RF coil 82 by a transmit/receive switch 88. The resulting signals emitted by the excited nuclei in the patient may be sensed by the same RF coil 82 and coupled through the transmit/receive switch 88 to a preamplifier 90. The amplified MR signals are demodulated, filtered, and digitized in the receiver section of the transceiver 84. The transmit/receive switch 88 is controlled by a signal from the pulse generator module 64 to electrically connect the RF amplifier 86 to the coil 82 during the transmit mode and to connect the preamplifier 90 to the coil 82 during the receive mode. The transmit/receive switch 88 can also enable a separate RF coil (for example, a surface coil) to be used in either the transmit or receive mode.

The MR signals picked up by the RF coil 82 are digitized by the transceiver module 84 and transferred to a memory module 92 in the system control 58. A scan is complete when an array of raw k-space data has been acquired in the memory module 92. This raw k-space data is rearranged into separate k-space data arrays for each image to be reconstructed, and each of these is input to an array processor 94 which operates to Fourier transform the data into an array of image data. This image data is conveyed through the serial link 60 to the computer system 46 where it is stored in memory, such as disk storage 54. In response to commands received from the operator console 38, this image data may be archived in long term storage, such as on the tape drive 56, or it may be further processed by the image processor 48 and conveyed to the operator console 38 and presented on the display 42.

The present invention will be described with respect an ECG gated, navigator gated FIESTA sequence played out for whole heart imaging for coronary artery assessment. As will be described below, MR images were reconstructed of a phantom based on data acquired with such a sequence. While such a sequence will be described, the present invention is not so limited. Moreover, while preferred that the present invention be carried out on an MR apparatus such as that described above with respect to FIG. 4, it is contemplated the present invention may be carried out on equivalent MR systems.

Figure 5:
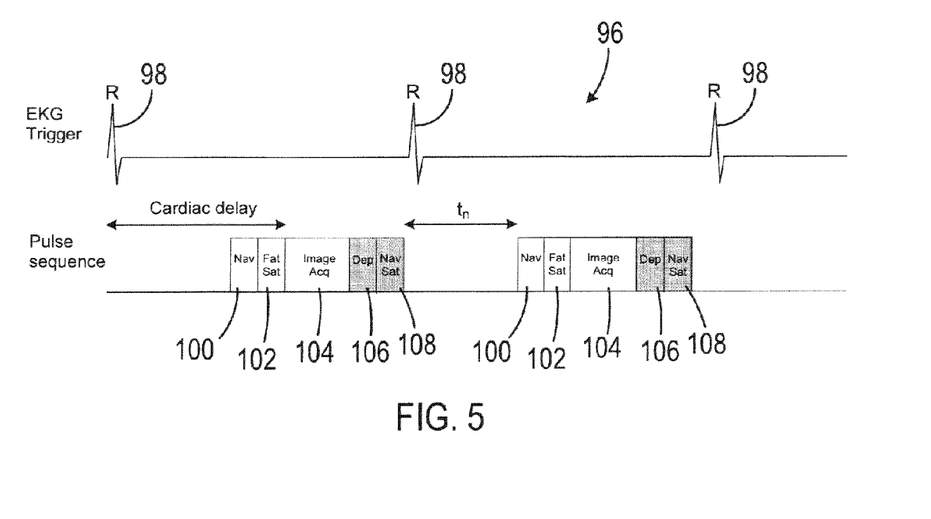
FIG. 5 illustrates a navigator saturation pulse sequence according to the present invention.

The present invention is designed to reduce the partial saturation effect on the navigator spatial profile described above by saturating the entire navigator profile at the end of the imaging acquisition segment thereby allowing uniform recovery of longitudinal magnetization for the next imaging period. A sequence diagram for a pulse sequence according to the present invention is illustrated in FIG. 5.

As shown, the pulse sequence is triggered by an ECG trigger signal 96 such that each imaging period is defined by R peaks 98. In this regard, the pulses and/or segments described hereinafter are played out each R-R interval. The pulse sequence, similar to that described with respect to FIG. 1, has a navigator excitation segment whereby a navigation RF excitation pulse 100 designed to excite spins within a navigator tracker of a patient is played out. Following pulse 100, a fat saturation pulse 102 is played out to suppress the signal from fat within the region of interest to be imaged.

Following fat saturation, an imaging acquisition segment 104 is played out to acquire MR data for a segment of k-space from the region of interest. After the segment of k-space is acquired 104, dephaser gradients 106 are applied in the x, y, and z directions to dephase any residual transverse magnetization in the navigator tracker. Immediately thereafter, a navigator RF saturation pulse 108, with a flip angle of ninety degrees, is applied to saturate spins within the navigator tracker to ensure a substantially uniform recovery of longitudinal magnetization for the next imaging period. Pulses 100-108 are then played out, as described above, in the next cardiac cycle. This reapplication of pulses 100-108 continues until k-space has been acquired. It is noted that the generally the tracker column or portion is positioned outside the region-of-interest containing the targeted anatomy for imaging. For example, for heart imaging, the tracker column is defined outside the heart.

The navigator RF saturation pulse 108 is similar to the navigator RF excitation pulse 100 applied before image acquisition. As a result of this saturation sequence, the residual magnetization heretofore that has been present after the imaging acquisition segment is reduced and all spins will recover to the same longitudinal magnetization value in the next heart cycle. Specifically:

$$M_z(t_n) = M_o(1 - \exp(-t_n/T_1))$$ (Eqn. 2), where $t_n$ is the time from the navigator RF saturation excitation to the navigator RF excitation in the next heart cycle. It is desirable to apply the dephaser gradients to prevent any residual transverse magnetization from rephrasing and evolving into longitudinal magnetization by the (ninety degree flip angle) navigator RF saturation pulse 108. Additionally, since the flip angle experienced by different regions of the navigator tracker may not be exactly ninety degrees (due to imperfections in the spatial excitation profile), the navigator saturation region preferably has a diameter larger than the navigator excitation region. The diameter of the navigator saturation region should be selected such that at least most of the spins within the region of interest will experience a full ninety degree flip angle. In one preferred embodiment, a diameter ratio of 1.5:1 is used.

Figure 6:
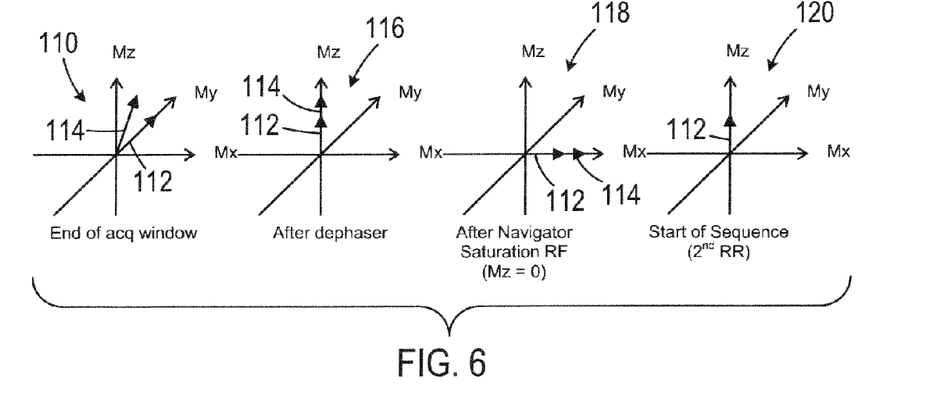
FIG. 6 illustrates the evolution of magnetization of overlapped and non-overlapped spins within a navigator tracker at different time points within two consecutive heart cycles resulting from application of the pulse sequence illustrated in FIG. 5.

FIG. 6 illustrates the magnetization of the overlapped and non-overlapped spins with the present invention. As illustrated, at the end of the acquisition window 110, the longitudinal magnetization of the overlapped spins 112 is less than the spins of the non-overlapped region 114. After the dephaser gradients have been applied 116, any residual transverse magnetization is dephased and all spins are aligned along the $M_z$ axis. As a result of the navigator RF saturation pulse 118, the overlapped and the non-overlapped spins are saturated such that $M_z=0$. As such, at the start of the next imaging period 120, the residual longitudinal magnetization has vanished and the overlapped spins have recovered. It should be noted that the "Start of Sequence" 120, FIG. 6, for the second RR is similar to the "Start of Sequence" 20, FIG. 1, for the first RR. Thus, as a result of the saturation sequence described herein, the spin magnetization at the end of the cycle is consistent with the spin magnetization at the beginning of the cycle.

Figure 7:
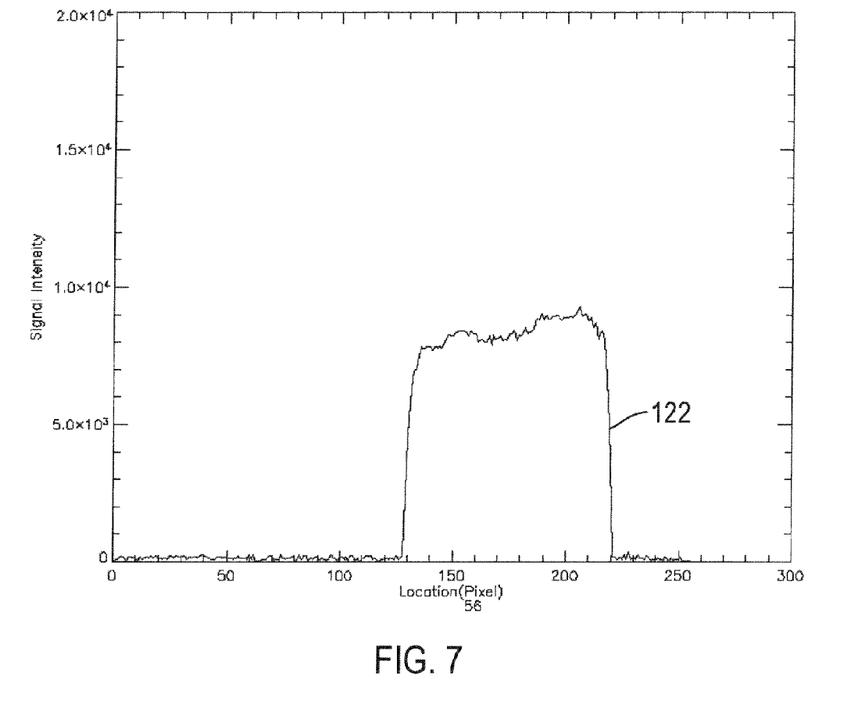
FIG. 7 is a signal intensity profile for the navigator tracker during the second heart cycle of two consecutive heart cycles resulting from application of the pulse sequence illustrated in FIG. 5.

Referring now to FIG. 7, a signal intensity profile 122 for the navigator tracker during the second heart cycle of two consecutive heart cycles resulting from application of the pulse sequence illustrated in FIG. 5 is shown. As illustrated, the profile 122 is more uniform compared to profile 32 of FIG. 3. That is, the saturation heretofore caused by the imaging slab has been eliminated. In other words, signal intensity is substantially uniform relative to the profile of FIG. 3.

As also illustrated in a comparison of the profiles of FIGS. 3 and 7, there is a difference in overall signal intensity of the navigator spatial profile. The reduction in signal intensity of the profile of FIG. 7 can be attributed to saturation of all spins at the end of the previous heart cycle as opposed to only part of the spins being saturated in the profile of FIG. 3. However, as motion detection techniques are generally sensitive to the presence of edge or the relative shift in the shape of the profile, a change in magnitude of the profile should have little impact on motion detection.

Testing of the pulse sequence illustrated in FIG. 5 was carried out on a GE SIGNA EXCITE 1.5T scanner (GE Healthcare Technologies, Waukesha, Wis.). SIGNA and EXCITE are registered trademarks of General Electric Co., Schenectady, N.Y. Images were acquired with an ECG gated, navigator gated FIESTA acquisition for whole heart imaging for coronary artery assessment. A water phantom was placed on the table of the scanner and the scanner was programmed to move the table in a sinusoidal motion in the superior/inferior (S/I) direction to simulate respiratory motion of a patient. A 2D-spatially selective navigator tracker (pencil beam) was prescribed at the superior boundary of the phantom along the S/I direction. A 3D image acquisition volume was prescribed as an axial plane and overlapped part of the navigator tracker. Sequence parameters for both the navigator excitation and the navigator saturation were a flip angle of ninety degrees, number of turns=12, diameter=2 cm, and tracker length=20 cm. The image acquisition parameters were a TR=4.4 ms, TE=2.0 ms, k-space matrix of 256×256, flip angle=60 degrees, TI=100 ms, 32 views per segment, 3 mm slice thickness, and 8 slices.

Navigator echoes were acquired at each heart cycle while the table was moving and motion profiles were detected using the conventional saturation technique illustrated in FIG. 1 and the navigator saturation technique of FIG. 5. The motion profiles were measured from the Fourier transformed spatial data of the navigator echo and the data were compared against the values calculated from the least-squares error minimization motion detection algorithm for both techniques. The results revealed that the accuracy of motion detection was improved with the saturation technique described with respect to FIG. 5. That is, the motion profile with the novel saturation technique described herein was substantially matched to the sinusoidal movement of the scanner table.

The present invention was also tested in a clinical setting for MR liver imaging. The navigator tracker was placed at the dome of the right hemi-diaphragm and the image acquisition volume was placed in an axial plane through the liver. The imaging plane was positioned to intersect with part of the navigator tracker. Navigator spatial data was acquired and revealed that the partial saturation effect induced by the overlapping imaging volume was greatly reduced with the saturation technique of the present invention.

While the invention is particularly applicable to cardiac gated FIESTA acquisitions, the present invention is applicable to other sequences that use a navigator echo for motion suppression. In addition, while particularly applicable to 2D spatially selective navigator excitation, the present invention is also applicable to spin-echo based navigator excitation, fat navigator excitation, and other navigator techniques.

Therefore, an MR imaging apparatus is disclosed and includes a plurality of gradient coils positioned about a bore of a magnet to impress a polarizing magnetic field and an RF transceiver system and an RF switch controlled by a pulse module to transmit RF signals to an RF coil assembly to acquire MR images. The apparatus also has a computer programmed to apply a pulse sequence during an imaging period of a free-breathing gated acquisition. The pulse sequence is defined by a navigator RF excitation pulse designed to selectively excite a tracker column and an image acquisition segment designed to acquire MR data. The pulse sequence also has a navigator RF saturation pulse designed to saturate the tracker column such that longitudinal magnetization recovery in the tracker column is uniform for a next imaging period.

The present invention also includes a method of MR imaging that includes the steps of (A) applying an RF excitation pulse to excite spins within a tracker portion of a subject to be imaged and (B) applying an imaging sequence to acquire MR data from a region-of-interest. The method further includes the steps of (C) applying an RF saturation pulse to saturate spins within the tracker portion after acquisition of the MR data and (D) repeating steps (A)-(C) in each cycle of a physiologically gated acquisition.

The invention is further embodied in a computer program stored on a computer readable storage medium and having instructions which, when executed by a computer, cause the computer to acquire tracking data from a motion tracker and acquire imaging data for a segment of k-space from a region-of-interest. The computer is further caused to suppress residual longitudinal magnetization in the motion tracker and repeat the acquisition of tracking data and imaging data and suppression of longitudinal magnetization every cycle of a gated acquisition until the necessary k-space is acquired.

The present invention has been described in terms of the preferred embodiment, and it is recognized that equivalents, alternatives, and modifications, aside from those expressly stated, are possible and within the scope of the appending claims.

What is claimed is:

1. An magnetic resonance (MR) imaging apparatus comprising:
   a plurality of gradient coils positioned about a bore of a magnet to impress a polarizing magnetic field and an RF transceiver system and an RF switch controlled by a pulse module to transmit RF signals to an RF coil assembly to acquire MR images; and
   a computer programmed to apply a pulse sequence during an imaging period of a free-breathing gated acquisition, the pulse sequence defined by:
      a navigator RF excitation pulse designed to selectively excite a tracker column;
      an image acquisition segment designed to acquire MR data from a region-of-interest; and
      a navigator RF saturation pulse designed to saturate the tracker column such that longitudinal-magnetization recovery in the tracker column is uniform for a next imaging period.

2. The MR imaging apparatus of claim 1 wherein the pulse sequence is further defined by at least one dephaser gradient designed to dephase residual transverse magnetization in the tracker column that is played out after the image acquisition segment and before the navigator RF saturation pulse.

3. The MR imaging apparatus of claim 1 wherein a spatial coverage of the navigator RF saturation pulse has a diameter greater than that of the navigator RF excitation pulse.

4. The MR imaging apparatus of claim 3 wherein the diameter of the spatial coverage of the navigator RF saturation pulse is 1.5 times greater than that of the navigator RF excitation pulse.

5. The MR imaging apparatus of claim 1 wherein the navigator RF saturation pulse has a flip angle of ninety degrees.

6. The MR imaging apparatus of claim 1 wherein the computer is further programmed to repeat the pulse sequence during each imaging period of a physiologically gated acquisition until all desired views are acquired.

7. The MR imaging apparatus of claim 6 wherein each imaging period is defined by an R-R interval of a cardiac cycle.

8. The MR imaging apparatus of claim 1 wherein the pulse sequence is further defined by a fat saturation pulse designed to saturate spins from fat in the region-of-interest, the fat saturation pulse played out after the navigator RF excitation pulse and before the image acquisition segment.

9. The MR imaging apparatus of claim 1 wherein the computer is further programmed to sample an echo excited by the navigator RF excitation pulse during the image acquisition segment and determine respiratory motion in the tracker column from the sampled echo.

10. The MR imaging apparatus of claim 1 wherein the computer is further programmed to acquire 3D MR data during the image acquisition segment.

11. A method of MR imaging comprising the steps of:
(A) acquiring navigator echo data elicited by an RF navigator excitation pulse applied to a tracker portion of a subject to be imaged;
(B) applying an imaging sequence to acquire MR data from a region-of-interest;
(C) applying an RF saturation pulse to saturate spins within the tracker portion after acquisition of the MR data;
(D) repeating steps (A)-(C) in each cycle of a physiologically gated acquisition; and
(E) reconstructing an image based on the acquired MR data.

12. The method of claim 11 further comprising the steps of acquiring MR data from the region-of-interest during free-breathing of the subject.

13. The method of claim 11 further comprising the step of applying a fat saturation pulse after step (A).

14. The method of claim 11 further comprising the step of applying x,y,z dephaser gradients after step (B).

15. The method of claim 11 wherein the physiologically gated acquisition is either a cardiac or a respiratory gated acquisition.

16. The method of claim 11 wherein the RF saturation pulse has a flip angle of ninety degrees and a spatial coverage that is larger than that of the RF navigator excitation pulse.

17. The method of claim 11 further comprising the step of defining the tracker position to have a location where physiological motion of the subject can be captured.

18. The method of claim 11 wherein the region-of-interest includes an abdominal/cardiac region of the subject.

19. A computer readable storage medium having instructions stored thereon that when executed by a computer cause the computer to:
acquire navigator tracking data from a navigator excitation region;
acquire imaging data for a segment of k-space from a region-of-interest;
suppress residual longitudinal magnetization in the navigator excitation region;
repeat the acquisition of tracking data and imaging data and suppression of longitudinal magnetization every cycle of a gated acquisition until k-space is acquired; and
reconstruct an image based on the imaging data.

20. The computer readable storage medium of claim 19 wherein the computer is further caused to retrospectively gate acquisition of the imaging data based on the navigator tracking data such that imaging data acquired during intervals between physiological motion is used for image reconstruction.

21. The computer readable storage medium of claim 19 wherein the computer is further caused to acquire imaging data during subject free-breathing.

22. The computer readable storage medium of claim 19 wherein the computer is further caused to suppress signal from fat in the region-of-interest prior to the acquisition of imaging data.

23. The computer readable storage medium of claim 19 wherein the computer is further caused to apply dephaser gradients in x,y,z, directions following the acquisition of the imaging data.

24. The computer readable storage medium of claim 19 wherein the computer is further caused to apply a navigator saturation pulse with a ninety degree flip angle to suppress the residual longitudinal magnetization in the navigator excitation region.

25. The computer readable storage medium of claim 24 wherein spatial coverage of navigator saturation RF pulse has a diameter 1.5 times greater than that of a navigation excitation pulse applied to excite spins in the navigator excitation region.

* * * * *